United States Patent
Truitt et al.

(10) Patent No.: US 7,587,097 B2
(45) Date of Patent: Sep. 8, 2009

(54) MAX ENTROPY OPTIMIZED RETINAL CAMERA

(75) Inventors: Paul Wiley Truitt, Albuquerque, NM (US); Peter Soliz, Albuquerque, NM (US)

(73) Assignee: Kestrel Corporation, Albuquerque, NM (US)

( * ) Notice: Subject to any disclaimer, the term of this patent is extended or adjusted under 35 U.S.C. 154(b) by 0 days.

(21) Appl. No.: 12/050,029

(22) Filed: Mar. 17, 2008

(65) Prior Publication Data

US 2008/0298756 A1      Dec. 4, 2008

Related U.S. Application Data

(62) Division of application No. 10/428,320, filed on May 1, 2003, now Pat. No. 7,433,532.

(60) Provisional application No. 60/377,069, filed on May 1, 2002.

(51) Int. Cl.
    *G06K 9/40* (2006.01)
    *G06K 9/54* (2006.01)
(52) U.S. Cl. .................... 382/254; 382/307
(58) Field of Classification Search .......... 382/117, 382/251, 253–254, 266, 274, 307; 341/108, 341/110; 348/606, 625; 351/200, 206; 396/18
See application file for complete search history.

(56) References Cited

U.S. PATENT DOCUMENTS

| | | | | | |
|---|---|---|---|---|---|
| 4,992,889 | A | * | 2/1991 | Yamagami et al. | 382/238 |
| 5,157,428 | A | * | 10/1992 | Sklar et al. | 351/206 |
| 5,748,243 | A | * | 5/1998 | Suzuki | 375/240.03 |
| 5,818,974 | A | * | 10/1998 | Kimura et al. | 382/270 |
| 6,456,787 | B1 | * | 9/2002 | Matsumoto et al. | 396/18 |
| 2003/0208125 | A1 | * | 11/2003 | Watkins | 600/473 |

* cited by examiner

*Primary Examiner*—Daniel G Mariam
(74) *Attorney, Agent, or Firm*—Janeen Vilven; Peacock Myers, P.C.

(57) ABSTRACT

An enhanced entropy camera provides enhanced image quality by utilizing a custom analog-to-digital conversion function. The analog-to-digital conversion occurs according to a custom non-linear quantization function that provides enhanced entropy in the digitized image, yet avoids the harsh artifacts that tend to arise in images quantized according to a maximum entropy function. A plurality of custom non-linear functions are made available for selection depending upon imaging conditions, such as light intensity, pigmentation of the retina, or the part of the retina being imaged. Each of the plural non-linear quantization function comprises a distinct non-linear look up table for each of plural bands (e.g., red, green, and blue color channels).

10 Claims, 24 Drawing Sheets
(3 of 24 Drawing Sheet(s) Filed in Color)

MAX ENTROPY OPTIMIZED RETINAL CAMERA

CROSS REFERENCE TO OTHER APPLICATIONS

This application claims benefit under 35 U.S.C. § 119(e) of provisional application No. 60/377,069, filed May 1, 2002, which is incorporated by reference herein, in its entirety, for all purposes. This application is a divisional of application Ser. No. 10/428,320, filed May 1, 2003 (now U.S. Pat. No. 7,433,532 issued on Oct. 7, 2008) which is incorporated by reference herein, in its entirety, for all purposes.

INTRODUCTION

This invention relates generally to enhancement of useful information content, or entropy, of digital images. More particularly, the present invention relates to imaging of blood perfused organs with a digital camera.

BACKGROUND OF THE INVENTION

Digital cameras and the associated digital imagery continue to replace film photography in opthalmology for archiving a patient's medical history and for preserving visual data in research of disease. Quantitative approaches for documenting the state of disease in longitudinal analysis and diagnosis can best be implemented using digital images. Unfortunately, the typical digital camera technology employed by the majority of clinics today has low resolution, low dynamic range, and otherwise poor performance with respect to retinal imaging. This has opened the market for high-priced solutions with multi-mega pixel format cameras employing 12-bit (or greater) color depth offering some improvement. Unfortunately these cameras are priced at $25,000 or more and are beyond the means of many eye clinics. The seriousness of the retinal image quality problem is reflected in discussions by renowned individuals in the fields of retinal reading and retinal disease epidemiology. These experts are acutely aware of the issues of current digital image quality. Experts in the field depend almost entirely on retinal images for their research, and would benefit from an enhanced entropy method and apparatus.

Referring now to FIG. 1, an interdependence of resolution and contrast for human perception is illustrated. The inverse contrast sensitivity, IC, is portrayed and corresponds to the formula shown, wherein $I_{obj}$ is the intensity of the object of interest, and $I_{Back}$ is the intensity of the image background. As the spatial features become smaller (higher spatial frequency), the contrast threshold (shaded area) for the ability of a human to detect the feature increases. In other words, the smaller the feature, the higher the contrast must be between it and the surrounding background. For applications like screening, where the lesions, such as micro aneurysms, may be quite small, it becomes valuable to have a retinal image with sufficient contrast so that early signs of diabetic retinopathy, which are usually smaller and more subtle than in later stages of the disease, may be correctly identified and diagnosed.

A common technique for improving contrast is to apply equalization (contrast stretching). Referring now to FIG. 2A an image scanned using standard settings for Nikon 35 mm slide scanner is illustrated. FIG. 2B illustrates the histogram presentation of the image in FIG. 2B. Referring now to FIG. 3A, an equalized version of the digitized image in FIG. 2A is illustrated. FIG. 3B illustrates the histogram representation of the equalized image in FIG. 3A. The increased contrast may be more appealing to the human observer and may even give the human analyst added visual cues when trying to detect certain lesions. Additionally, this processing of the image will improve the performance of some segmentation algorithms. However, for the inherent differences between tissue color and brightness that fall below the threshold allowed by the digitization scheme, these differences cannot be represented in the digital image. Furthermore, standard histogram equalization does not improve the ability to detect features not captured by the initial digitization. Histogram equalization merely takes the information in the digital image and re-maps it so the human eye can better visualize it.

Histogram equalization does not add information. For example, a typical color image is digitized using 24-bits. That is, each color channel (red, green, and blue) is digitized using 8-bits. 8-bits ($2^8$) equates to 256 gray levels of brightness or intensity for each color channel. This means that any difference in intensity less than $1/256^{th}$ of the dynamic range of the digitizer cannot be resolved. The dynamic range of the system is the maximum minus the minimum measurable flux of the sensing and electronics of the instrument.

In many applications where contrast may be low or where it has large variations, which is the case in retinal imaging, one can take advantage of certain features in the intensity histogram to maximize the use of the 256 gray levels allowed by the 8-bit digital representation. The histogram in FIG. 2B illustrates the point that many of the image pixels have intensities that lie in a very narrow range resulting in a low contrast. One implication of these data is that the gray levels are wasted in that they are not storing any information about the intensity levels in the image.

FIG. 3B illustrates the histograms for the image equalized. The histogram equalization has simply spread the gray levels so that the eye can better perceive them, but has not changed the fact that many of the gray levels are still not storing any information about the image and that the subtle scene intensity variations corresponding to these missing gray levels were not captured by the imager.

Several reports have proposed that a 4K×4K pixel color camera is necessary to achieve image quality found in 35-mm color slides. Human perception involves both the effects of resolution and contrast on lesion detection. By increasing contrast of lower resolution digital images, one can achieve results comparable to those of the traditional large-format cameras at a fraction of the cost. A 4K×4K color camera is very expensive. Integrating an enhanced entropy image quantizer with a 2K×2K or 1K×1K camera, such as the Spot Color RT ($13,000), would significantly reduce the cost and make digital imaging cost competitive with film photography without loss of sensitivity or specificity for screening of subtle retinal lesions. It is noted that the "K" quantity as used in this application is not intended to mean a factor of $10^3$ per se, but is meant to be approximately that amount so as to include within its meaning at least the computer science meaning of K=1024.

For many applications in opthalmology, including general-purpose clinical screening and telemedicine, fundus images must be digitized for transmission. For purposes of screening and diagnosis, the digital imager should be of sufficiently high quality (spatial resolution and contrast) to perform specific functions in diagnosing retinal diseases. Information will be lost in the digitizing process due to spatial sampling and intensity level quantization. Quantization is the bracketing of ranges of an analog signal to correspond to a particular digital number. The lost spatial information limits the spatial resolution, while the lost intensity information results in reduced contrast. The information lost through this quantization can never be recovered by processing. Automatic non-uniform gain control techniques have been proposed which will minimize the loss. However, none of these cameras attempt to improve the exposure where the scene varies as much and has such a highly unbalanced color (hue and saturation) as a blood-perfused organ, for example, the retina. Video or photographic images that are never digitized, but are presented for human viewing, suffer a similar loss. The human vision system can perceive about 60 to 100 distinct gray levels under typical viewing conditions. It is desirable that the digital image contain at least this amount of unique information. Ophthalmic imaging can be well-served by a system that can adjust the analog signal to maximize the information content of the digital image. For clinical applications, this adjustment should be automatic, and should adapt smoothly and robustly to changing retinal illumination and naturally occurring variations in retinal pigmentation among individuals.

As with any new medical imaging modality, changes in sensitivity and specificity for diagnosing disease may result. An enhanced entropy image method for obtaining higher contrast images would provide greater visual insight. A reasonable degree of agreement should occur when film-based images and entropy enhanced digital images are compared. There is a need for high quality digital imaging to supplement or perhaps eventually replace 35-mm photographs.

To meet this challenge an enhanced entropy camera is needed that takes advantage of low cost technologies (such as 8-bit digital cameras), but implements improvements through smarter use of the available quantizer to better sample the light reflected from the subject.

SUMMARY OF THE INVENTION

For ease of explanation, the present invention is explained below mostly in terms of method and apparatus that is being applied to imaging of the retina. However, the applicability and scope of the present invention goes well beyond this illustrative application. Enhancing the information content (or entropy) of an image being digitized has utility independent of what the content of the image is (i.e., the subject) or what structures or methods were used to capture the image.

The use of the method of the present invention has far reaching implications separate and apart from the application to human physiology. For example, there is a long history in the intelligence community of using aerial and space-based imagers for both national defense and environmental concerns. In the national defense arena, camouflage has been used to conceal troop locations and equipment from aerial view. Such camouflage relies upon presenting a normal vegetative or other blending color (e.g., tan for a desert environment) to a camera system in the hopes that the camouflage will not be noticed. However, camouflage does not reflect light in certain spectral ranges, notably the near IR range of 700-1100 nm. If a sensor is fielded with a sensitivity range that reaches into the near IR region, the customized LUT of the present invention may be selected particularly for enhancing detection of such camouflage.

More sophisticated camouflage mechanisms more closely mimic natural vegetation. However, where this is the case, the camouflage does not exactly mimic such vegetation. In such cases it is sometimes possible to obtain a sample of the camouflage in use, spectrally analyze the material and construct a customized LUT that takes advantage of the differences between the spectral characteristics of natural vegetation and that of the artificial camouflage.

The United States is a major exporter of agricultural products. For example, in the year 2001, the US exported agricultural products all over the world worth in excess of $53 Billion. These products have spectral characteristics that vary by species during the growing season. Each plant type has its own spectrum which, although variable within the plant type, has a general characteristic that can be used to judge the health of the plant type during the growing season. Knowledge of healthy plant spectra leads to use of the method of the present invention to customize a LUT to image plant types to determine health versus less healthy plants. This information in turn can be used to trigger application of corrective measures regarding irrigation or pest control to maximize yield.

Image enhancement according to the present invention is also useful in the field of mineral exploration. It is also the case that minerals have a spectrum that is characteristic of the presence of good, and bad, chemicals. To the extent that the spectra of interest and regions within those spectra can be characterized, custom LUT's peculiar to the chemicals of interest can be identified and used to explore quarries (in a terrestrial mode) or other areas from aerial or space borne sensors. Such sensors would take advantage of not only reflected energy but emitted energy, such as the case of near, mid-wave, and long wavelength IR sensor systems.

The present invention is useful to improve the image quality for any bit-depth digital camera, including, but not limit to, humble 8-bit digital cameras and, considering the typical quality of images produce with an 8-bit digital camera, the improvement can be substantial. Professional and consumer grade digital camcorders and digital still cameras, as well as traditional and low bandwidth television cameras and video phones, are examples of digital (8-bit or otherwise) imaging technology that can benefit substantially from aspects of the present invention, including custom quantization look up tables and custom spectral channel enhancement.

In summary, the techniques of the creation of the customized LUT's of the present invention are useful in multiple ways in a wide variety of economically or defense related industries and applications.

The term "entropy" as used in this disclosure refers to information content in a broad sense and is not meant to be limited to a narrower meaning according to a strict mathematical definition. The term "enhanced entropy" does not refer to a strict sense effort to maximize entropy for an image, but rather, is meant to refer to a balanced approach to image improvement where putting more information into the digital image is balanced with the consideration of ensuring that the image information is useable for interpretation via human vision and/or automatic segmentation and classification.

One embodiment of the present invention comprises a version of an 8-bit digital camera used in retinal imaging that has been modified to allow programming of an internal analog to digital (A/D) converter. A custom non-linear look-up table (LUT) is selected and loaded to obtain "high quality" images with the 8-bit digital camera. It is an aspect of the present invention to improve the ophthalmologist's ability to detect early signs of disease.

Another embodiment of the present invention comprises a traditional 16-bit digital camera and a custom non-linear LUT to re-quantize the resulting 16-bit image to an enhanced 8-bit image for display and/or compression for storage or transmission.

A camera embodied according to the present invention provides enhanced image quality by utilizing a custom analog to digital conversion function. A camera according to this aspect of the present invention is based on, for example, existing 8-bit digital cameras that are modified to capture high entropy and high contrast color images. The invention is not limited to 8-bit digital camera applications, and certainly may be advantageously embodied with 12-bit, 16-bit, or n-bit digital systems. The examples of modifying economical 8-bit digital cameras are used in this application since image enhancement is most evident in such low intensity-resolution systems.

One embodiment of the present invention is a low-cost, high-resolution, high-contrast color digital camera for opthalmology that is effective in meeting the digital image quality requirements of both general clinical screening and telemedicine in the assessment of diabetic retinopathy. Another embodiment of the present invention embodies a modified 1K×1K 8-bit digital CCD camera. The camera may be "color," it may be single band, or it may be generally n-band, with $n \geq 2$. An internal A/D converter is programmed to specifically implement a desired LUT that improves the gray-level representation of the retina. Each individual color band employs its own specific custom LUT. Generally speaking, each band will have an LUT that is distinct from those of the other bands, however, this distinctness is not strictly required to practice the invention and some portion of the bands may have identical LUT's.

Yet another embodiment of the present invention implements a programmable A/D that will allow one to select an appropriate one of plural custom LUT's based on pigmentation of a blood perfused organ (e.g., the ocular fundus), a particular region of tissue to be examined, or a particular type of lesions being targeted for identification.

One aspect of the present invention creates images that are useful in assessing the onset or presence of diabetic retinopathy, macular degeneration, or other eye diseases. The application of this invention is not limited to eyes, though, and may be used for picking any hard to detect features of an image. Generally, this invention is useful for imaging biological structures including humans, animals, and plants, either externally or internally. Image enhancement according to the present invention is also useful for generalized image sensing, such as satellite imaging, aerial imaging, and remote sensing.

A modified (enhanced entropy) camera as described in one embodiment of the present invention exploits recent technological advances in high sensitivity charge coupled device (CCD) cameras, and programmable digital signal processors (DSP). Other examples of image capture devices that are suitable for practicing the invention are complementary metal oxide silicon (CMOS) and infrared (IR). This invention is also compatible with technologies such as on chip processing, custom masks, variable pixel size, and pre-filtering of the incoming light. These structures are given as examples, and are not limiting of the structures via which the present invention may be practiced.

Current digital cameras suffer from several deficiencies. For example, today's low-cost CCD cameras do not have the dynamic range to image the human retina. The human retina is characterized by regions of high red spectrum reflectivity (20-40%) from the optic disc, and very low blue spectrum reflectivity (<2%) from the macula and fovea. Today's digital cameras process each of the color channels in the same manner and do not consider the special, red-saturated characteristics of the retina. The large variation in retinal characteristics (blonde versus brunette) in the population exacerbates the difficulty in obtaining high image quality. An improved (enhanced entropy) camera described in one embodiment of the present invention offers significant improvement over known digital cameras by addressing each of the deficiencies mentioned above.

Additional objects and advantages of the present invention will be apparent in the following detailed description read in conjunction with the accompanying drawing figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
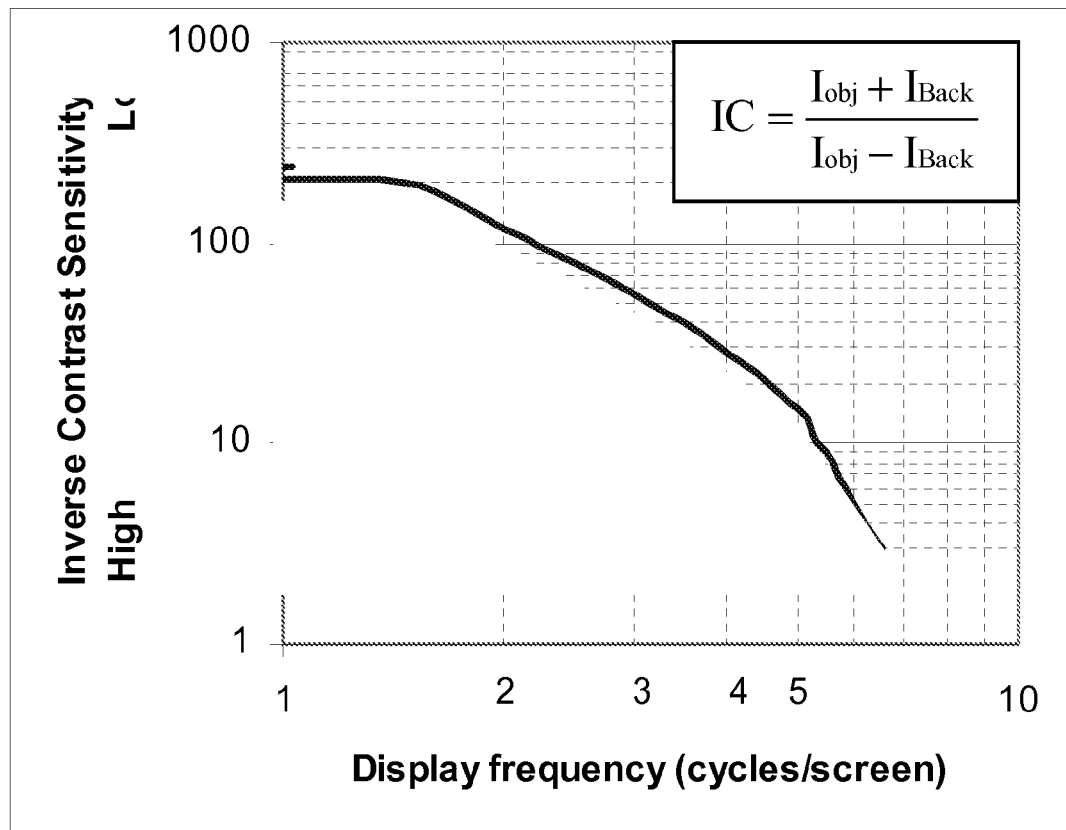
FIG. 1 illustrates the interdependence of resolution and contrast for human perception.
Figure 2A:
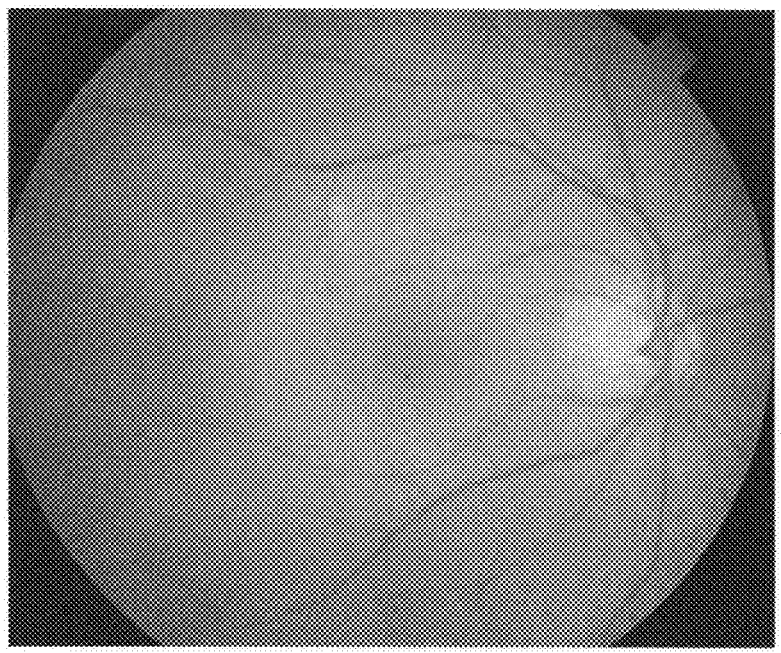
FIG. 2A illustrates an image scanned using standard settings for Nikon 35 mm slide scanner.
Figure 2B:
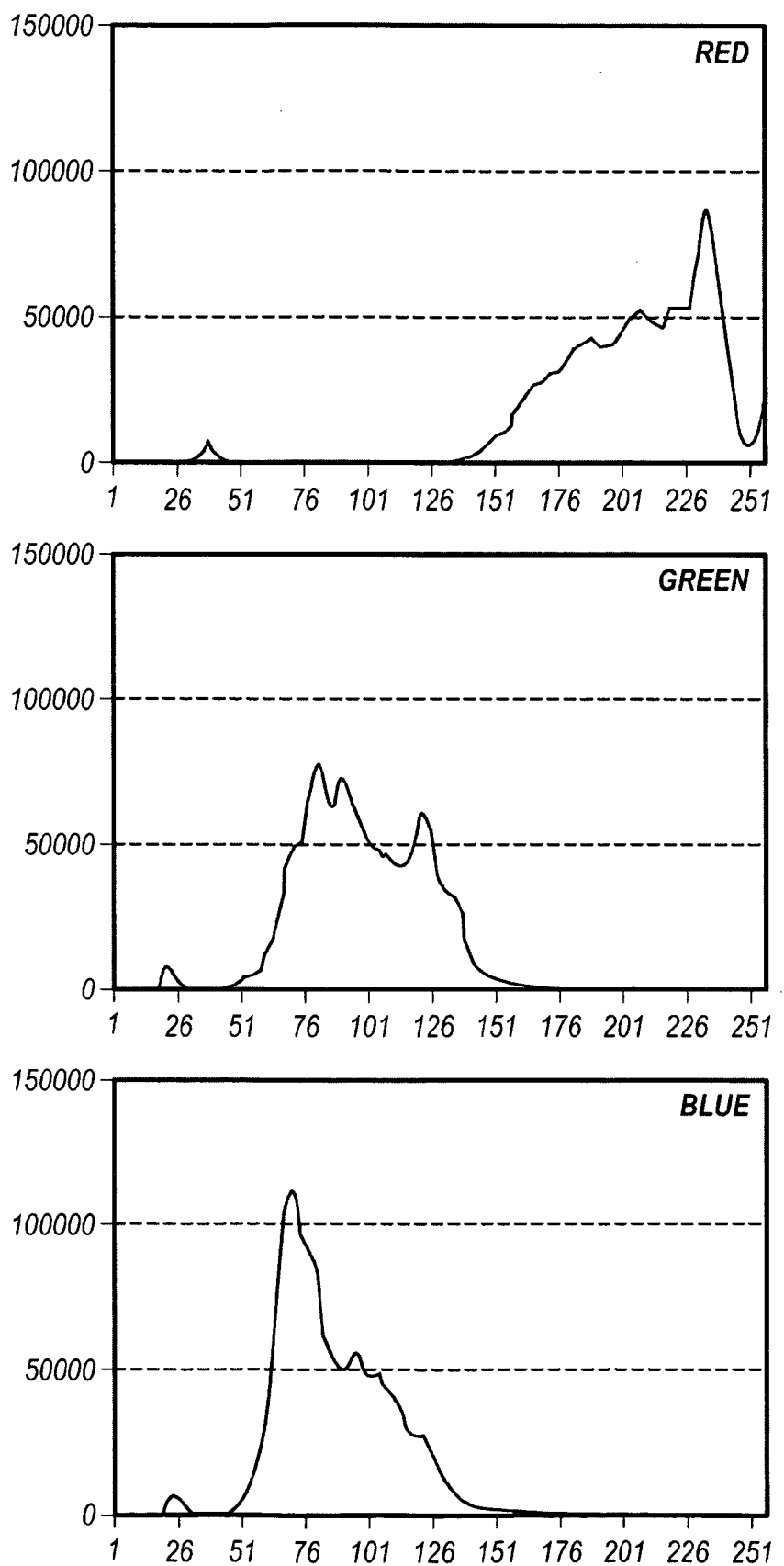
FIG. 2B illustrates an intensity histogram for the image in FIG. 2A.
Figure 3A:
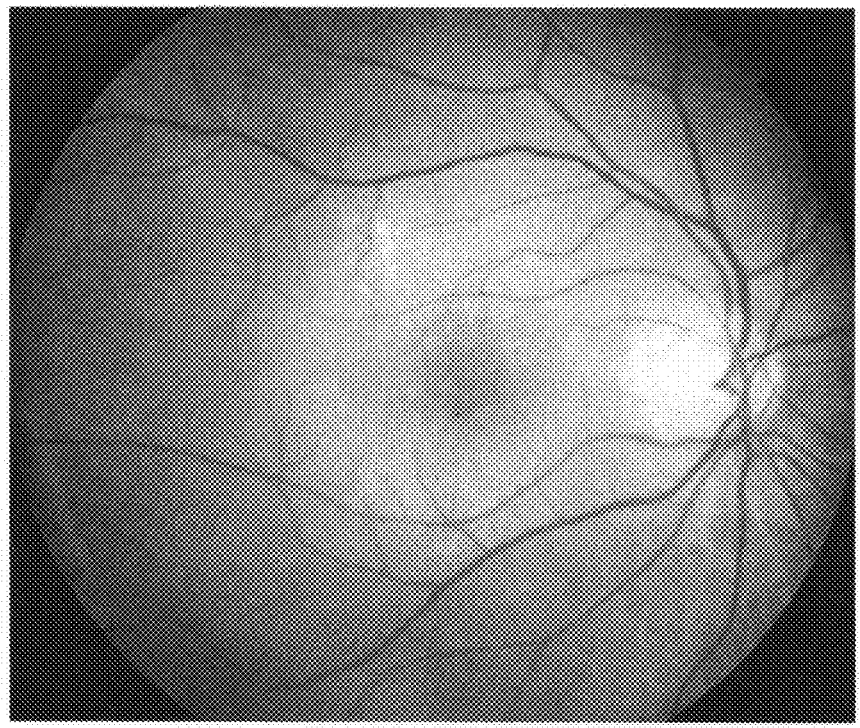
FIG. 3A illustrates a histogram equalized presentation of the image in FIG. 2A.
Figure 3B:
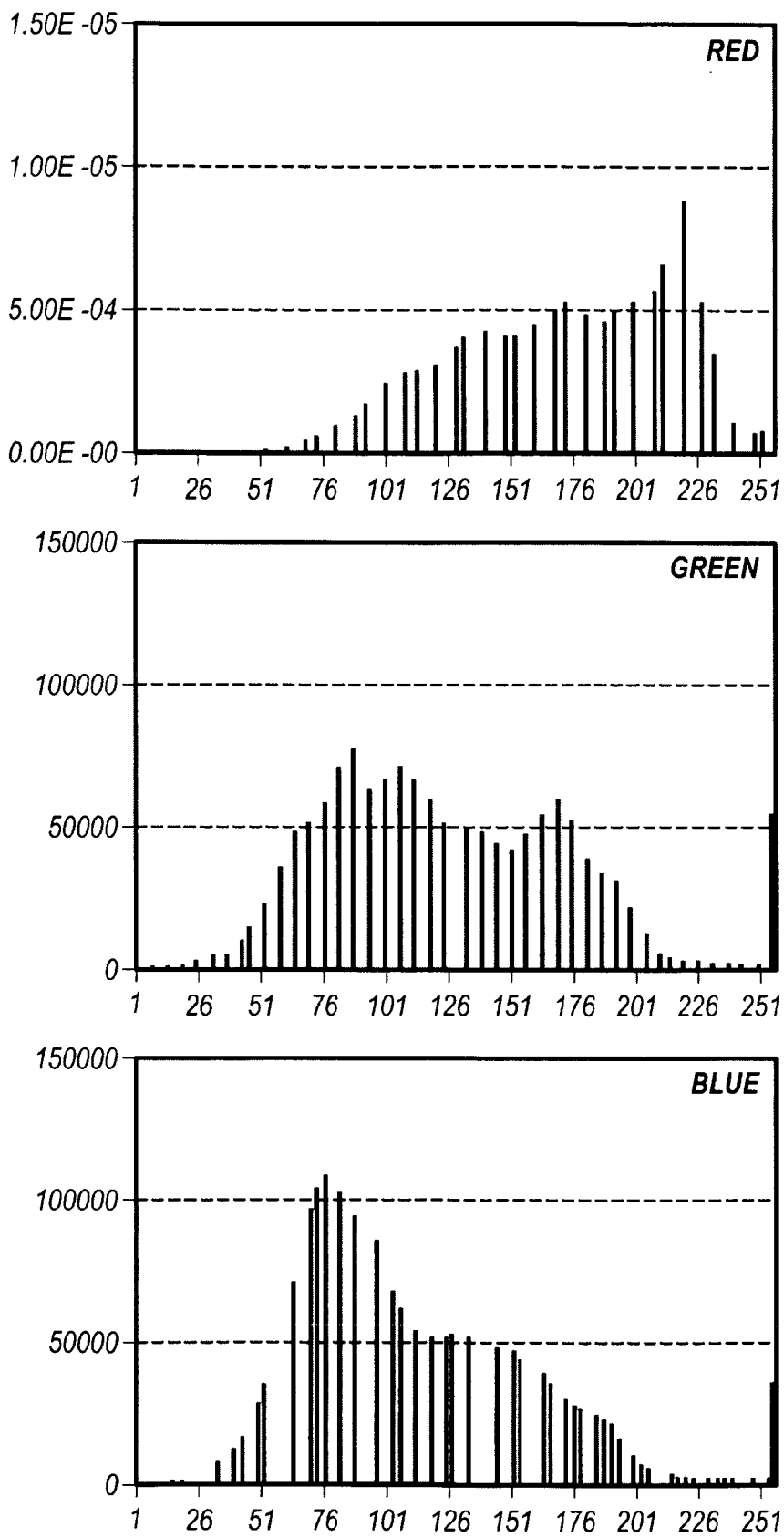
FIG. 3B illustrates an histogram of the equalized image in FIG. 3A.
Figure 4A:
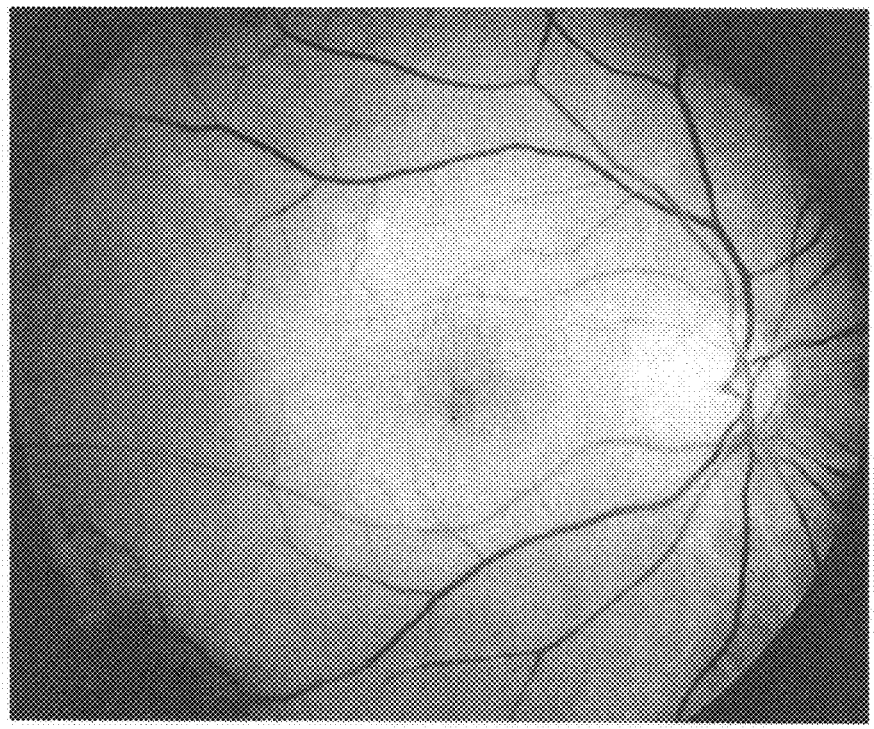
FIG. 4A illustrates an image as in FIG. 2A that has been digitized with an adjusted look up table to improve the information content.
Figure 4B:
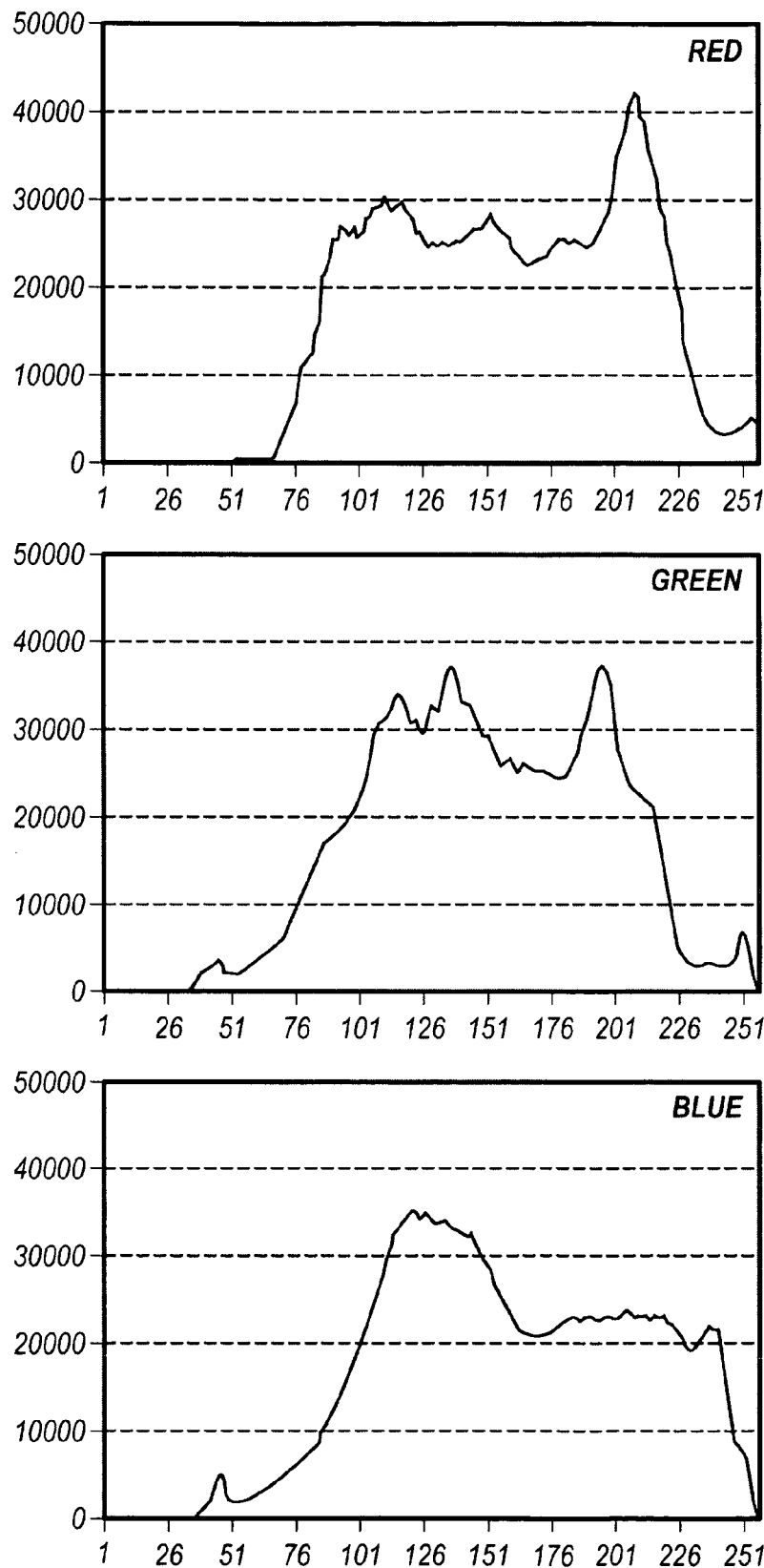
FIG. 4B illustrates a histogram for the image as illustrated in FIG. 4A.

By changing the manner in which the image is quantized by the analog to digital converter to make beneficial use of all 256 gray levels per channel, it is possible to store information about the more subtle (less than $1/256^{th}$ differences in brightness) levels of intensity. It has been described that a transform can perform the equalization of the analog signal, i.e. before these less than 1/256$^{th}$ differences are lost in the digitization. FIG. 4A illustrates the image in FIG. 2A when digitized with an improved look-up table. The image appears similar to the histogram-equalized image in FIG. 3A. Note however, that the resulting histograms, given in the inset of FIG. 4B, illustrate that more of the gray levels (entropy=5.2 bits) are storing information. Entropy is a measure of information content and represents how many bits of information are actually present. This means that some of the subtle differences in brightness levels lost in the original linear digitization of the image in FIG. 2A have been retained with the improved look-up table and are stored in the 256 levels of information representation. The ratio of gray levels used between FIG. 4A and FIG. 2A is 2.0. More than 2 times the number of gray levels are being used to store information (contrast) in FIG. 4A.

The LUT is a function that relates the analog voltage level produced by each given intensity and the corresponding digital number (DN) after digitization. The linear LUT is a straight line lying at 45° between voltage (scene intensity) on the vertical axis and DN on the horizontal. The linear LUT maps the lowest possible imager voltage to 0 and the highest possible to 255 (assume an 8-bit digital imager), regardless of the actual intensities present in the image. The shape of this LUT can be changed to accentuate certain voltage ranges that correspond to scene intensity data. This is referred to as non-linear gain control. This technique underlies the image enhancement of the present invention.

One aspect of the present invention is an improved contrast afforded by the enhanced entropy non-linear gain control to reduce the imager's spatial resolution and achieve lower-cost, high-quality color digital retinal images. Another aspect of the present invention is a capacity to integrate with a lower-cost 1K×1K detector with an 8-bit programmable analog to digital converter. This A/D converter is programmed with a custom non-linear LUT that has been constructed to produce images of highly readable subjective quality.

Research for the present invention identified a custom analog to digital conversion function, known as a look-up table (LUT) that produces real-time digital fundus images of improved visual quality. The LUT is responsible for the conversion of the analog voltage signal to a digital number in the quantization process. Standard digital cameras employ a linear LUT that maps the entire potential voltage range across the range of digital numbers equally. While most general-case scenes produce analog signals throughout the voltage range, the extreme conditions present in retinal imaging result in images with the majority of the data existing in a limited voltage range. Thus, the linear LUT does not utilize the majority of the available digital numbers in regions with no signal. Since digital numbers are limited by the dynamic range of the A/D converter (256 levels in the case an 8-bit digital camera), wasting such values on areas of no signal unnecessarily limits the number of values that are available for representing signals that are of interest. This limited number of available digital values results in loss of detail and contrast in the data region of the signal.

One aspect of the present invention is to make better use of the available digital values, and thus improve image detail and contrast. Further, since 8-bit quantizers are the most cost-effective and display technology readily exists for 8-bit image data, a custom LUT that maps to 256 digital levels is also desirable. Another aspect of the present invention is to provide customized non-linear look up tables for different pigmentation, target tissue and/or lesions. In order to determine the custom LUT's that produce the most visually informative digital images, numerous candidate LUT's were applied and the resulting digital images ranked by qualitative comparison. The LUT for the highest ranked image was selected for the given target tissue.

The maximum entropy LUT will produce the image with the maximum amount of information and contrast. The maximum entropy LUT accomplishes this by producing a uniform distribution of intensity values across the image (a uniform image histogram). Although the various digital numbers are optimally used, and the contrast in the image is high, the resulting image may not be well suited for the human perception (vision) system. That is, it is not "pleasing to the eye" and is, thus, qualitatively deficient. Maximum entropy images often appear grainy and stark, and although overall image contrast may be high, contrast between desired scene features may not. Initial investigative work illustrated that human graders routinely discount the image with maximum entropy, preferring instead an image with a slightly non-uniform (and non-maximum entropy) distribution. Thus, a desired custom LUT has been discovered between the linear LUT and the maximum entropy LUT. The linear LUT image has been used in investigations as a control, representing a "standard" image.

WORKING EXAMPLE

To simulate a continuous analog signal and to facilitate exploring the various candidate custom LUT's, 16-bit image data was used to represent an analog image scene. Although 16-bit images are already digitized, the vast increase in the number of quantizer levels, 65,536 for 16-bit verses 256 for 8-bit, produces data that is reasonably continuous. These 16-bit images were then resampled using the custom LUT and an 8-bit candidate image produced. This process was repeated for each candidate LUT. The resulting candidate 8-bit images were then compared and ranked based on a subjective quality assessment.

Subject data was collected using a specialized 16-bit, thinned, back illuminated Roper digital camera mated to a Zeiss FF5 fundus camera. The Roper digital camera has a format of 1340×1300 pixels, high (85%) quantum efficiency across the optical wavelength band of interest, and is liquid nitrogen cooled to −100 degrees C. to have extremely low noise. Interference filters were inserted between the FF5 and the digital camera to allow collection of specific spectral bands.

The subject fundus was imaged at 45 degrees centered half way between the optic disc and macula. Both the disc and macula were included in the field of view. Images were sequentially collected with filters corresponding to the red, green, and blue (RGB) channels of traditional color film. Additional images were collected at a variety of 10-nm wide bands across the visible region of the spectrum. The red, green, and blue images were collected with the same flash setting for a given subject. This setting varied depending upon fundus pigmentation. Additional red, green, and blue images were acquired independently with different flash settings chosen so as to improve each channels exposure, respectively. All narrow-band (10-nm bandwidth) images for all subjects were collected at the maximal flash setting. All images were then manually registered. All subjects underwent dilated examination. Color film of the seven standard fields was taken of each subject.

For purposes of the study of this imaging embodiment, volunteers are selected who are at least 18 years old who are initially willing to participate in the study to its completion. One group of participants (the control group) has no pathologic conditions of their eyes, although some may be pseudophakic. The main group of participants with pathologic conditions of the eye have varying degrees of diabetic retinopathy, with the focus primarily on non-proliferate, or, background, diabetic retinopathy.

Testing of individuals with media opacities (cornea, lens, vitreous) that would limit the ability to clinically view the fundus, and thus are not good candidates for study, are excluded. Individuals whose pupils do not dilate to at least 7 mm in diameter, or, whose pupils cannot be dilated due to significant risk of angle-closure glaucoma are also not suitable test subjects.

Figure 5:
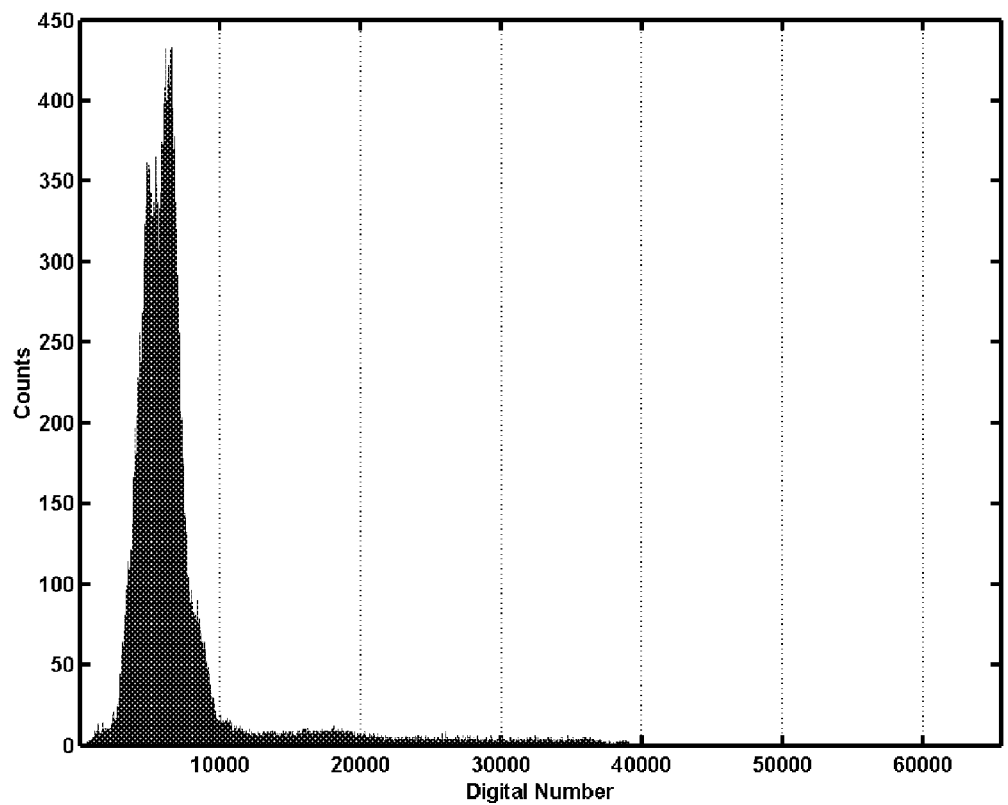
FIG. 5 illustrates a histogram of an original 16-bit green channel image.

Referring now to FIG. 5, a histogram from a 16-bit green channel image (collected through a green filter) from a normal subject is illustrated. The vast majority of information is contained in the lower 10,000 digital numbers, with the remainder of the 65,536 values representing little information.

Figure 6:
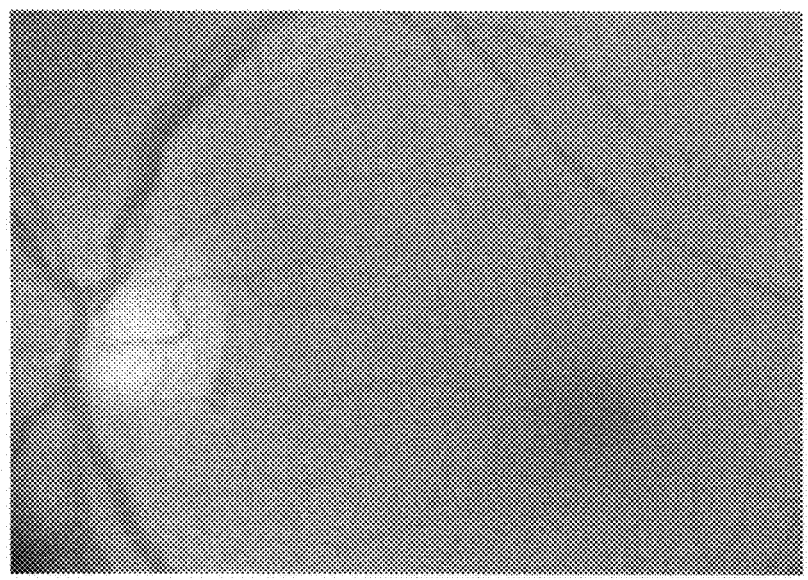
FIG. 6 illustrates an 8-bit digital camera image resulting from a linear LUT.
Figure 7:
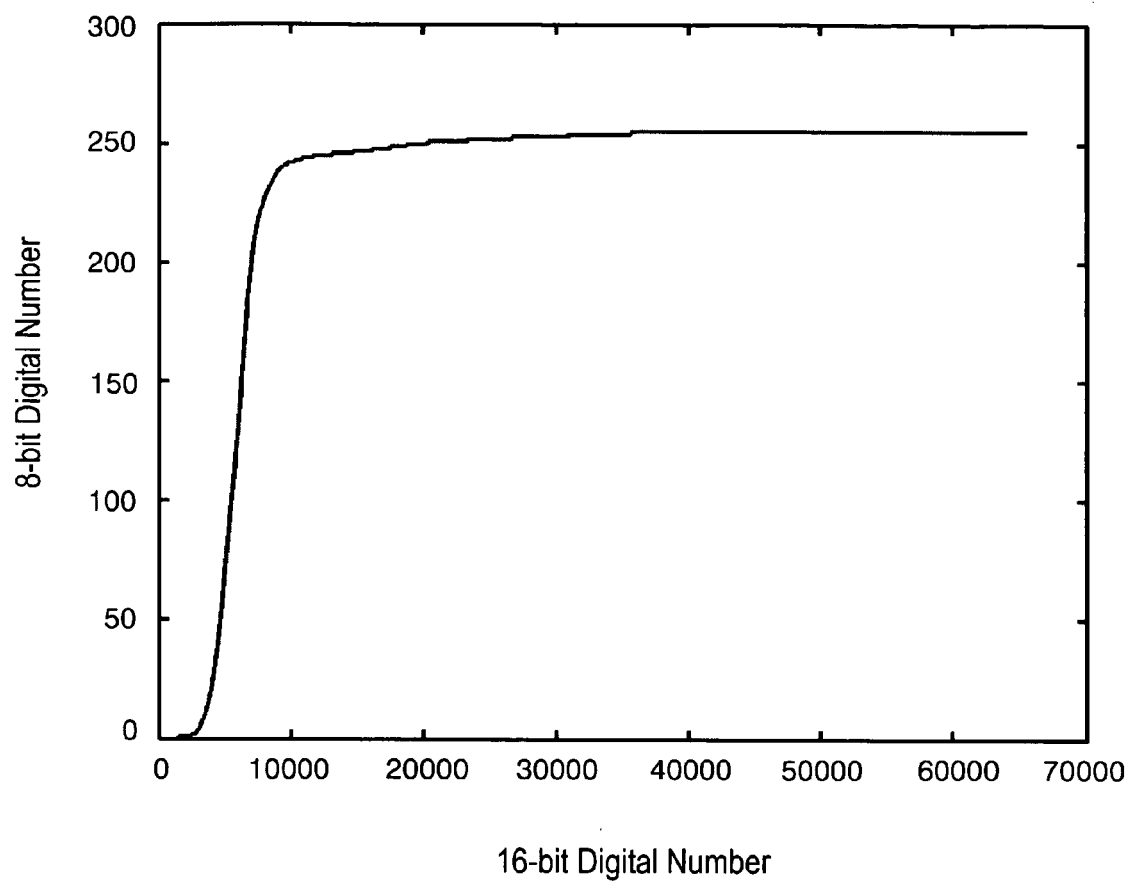
FIG. 7 illustrates the function for a maximum entropy non-linear look up table for an original 16-bit image.
Figure 8:
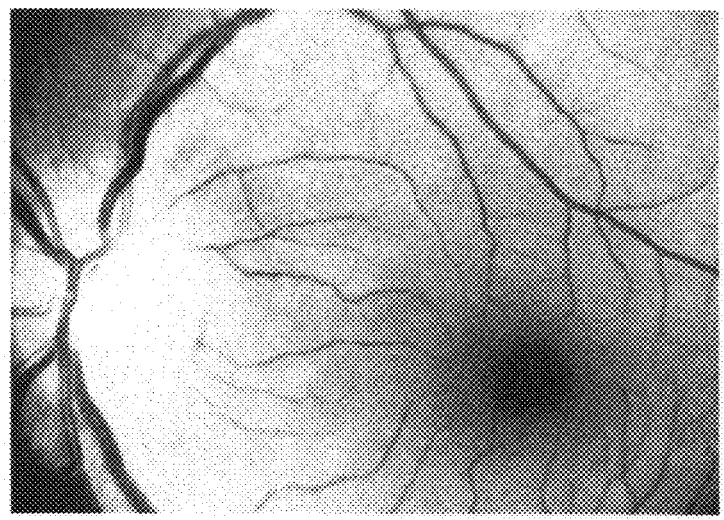
FIG. 8 illustrates an 8-bit digital camera image resulting from digitizing using a maximum entropy non-linear look up table.
Figure 9:
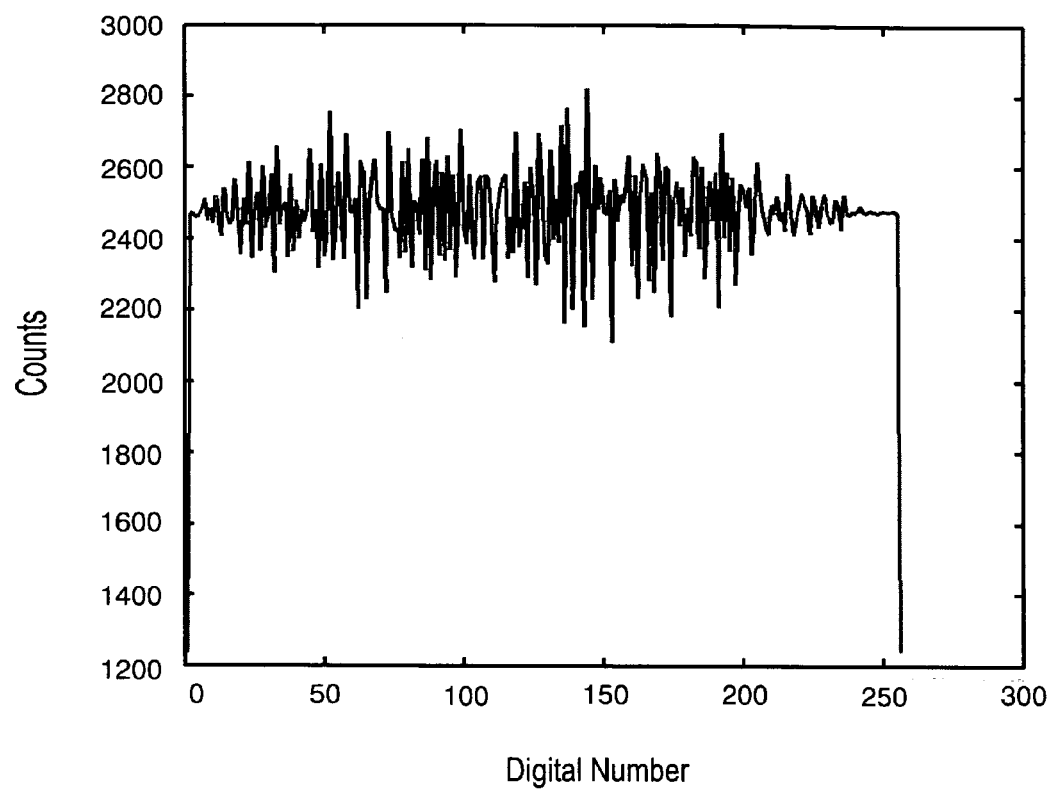
FIG. 9 illustrates the histogram of the 8-bit digital camera enhanced entropy image of FIG. 8 obtained using a maximum entropy non-linear look up table.

Referring now to FIG. 6 is the corresponding 8-bit digital camera image produced using the linear LUT function employed by traditional digital cameras. This image has been further histogram equalized for printing purposes. Note that the image is in general dark, with limited contrast. In subjective comparisons, this linear image was ranked low on a scale of relative quality.

To identify an effective LUT for use for the custom non-linear quantization function, human graders are used according to an exemplary embodiment. This ensures that the selected LUT provides images that are compatible with human vision. As an example of how this has been accomplished, the custom function is arrived at by selecting the most appealing 8-bit mapping from the 16-bit data from among several candidate images produced using custom LUT's and compared. The search was bounded by the linear mapping function and the maximum entropy function. These variations were limited to those that produce legitimate mappings (monotonic non-descending functions). Details of the process for obtaining selection of look up tables based on the choices of human graders is set forth at length in provisional application No. 60/377,069, filed May 1, 2002, which is incorporated by reference herein. The results of such human preference can be combined to form a metric which may then be used automatically identify the preferred custom non-linear LUT based on a given analog scene. Such a metric is then useful for efficiently identifying custom non-linear LUTs for different image types or in a camera employing a dynamic custom LUT.

Figure 10:
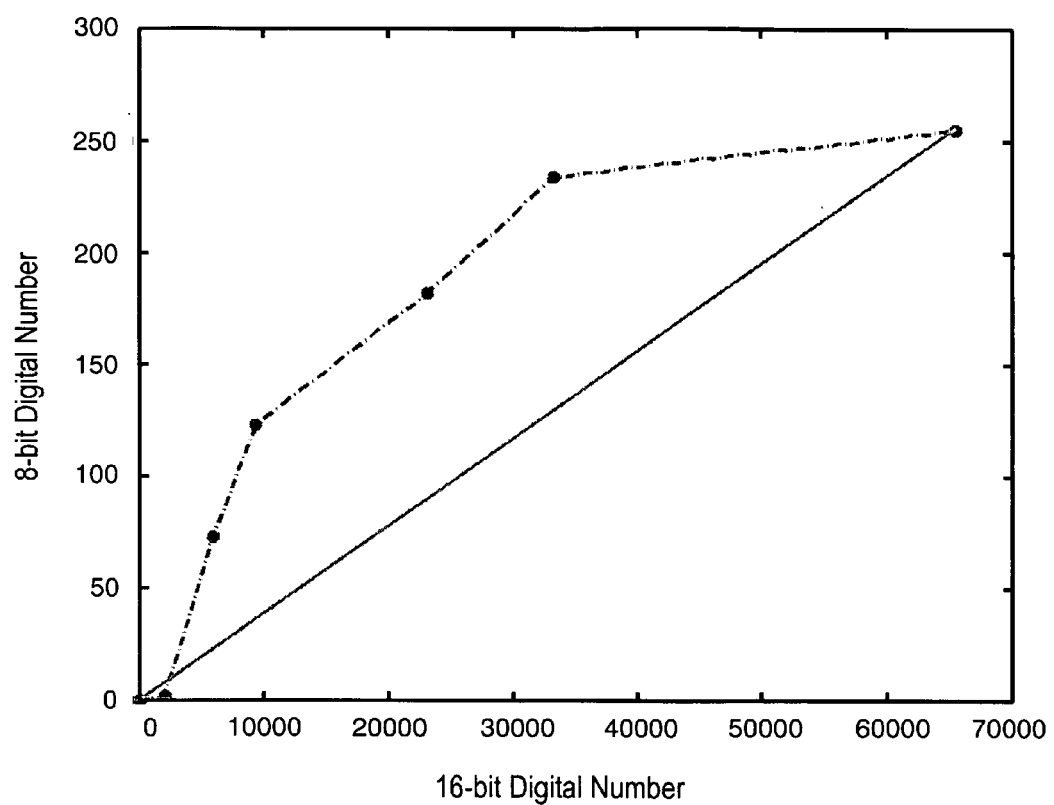
FIG. 10 illustrates a custom non-linear look up table according to an embodiment of the present invention (dashed) compared with a linear look up table (solid).

Referring now to FIG. 10 the LUT function for a selected candidate image is illustrated as a dashed line. The linear LUT function is illustrated as a solid line.

Figure 11A:
FIGS. 11A-11D illustrate the image and digitized according to a custom LUT of the present invention and its histogram, compared with those for a traditional linear LUT image of the same subject.
Figure 11B:
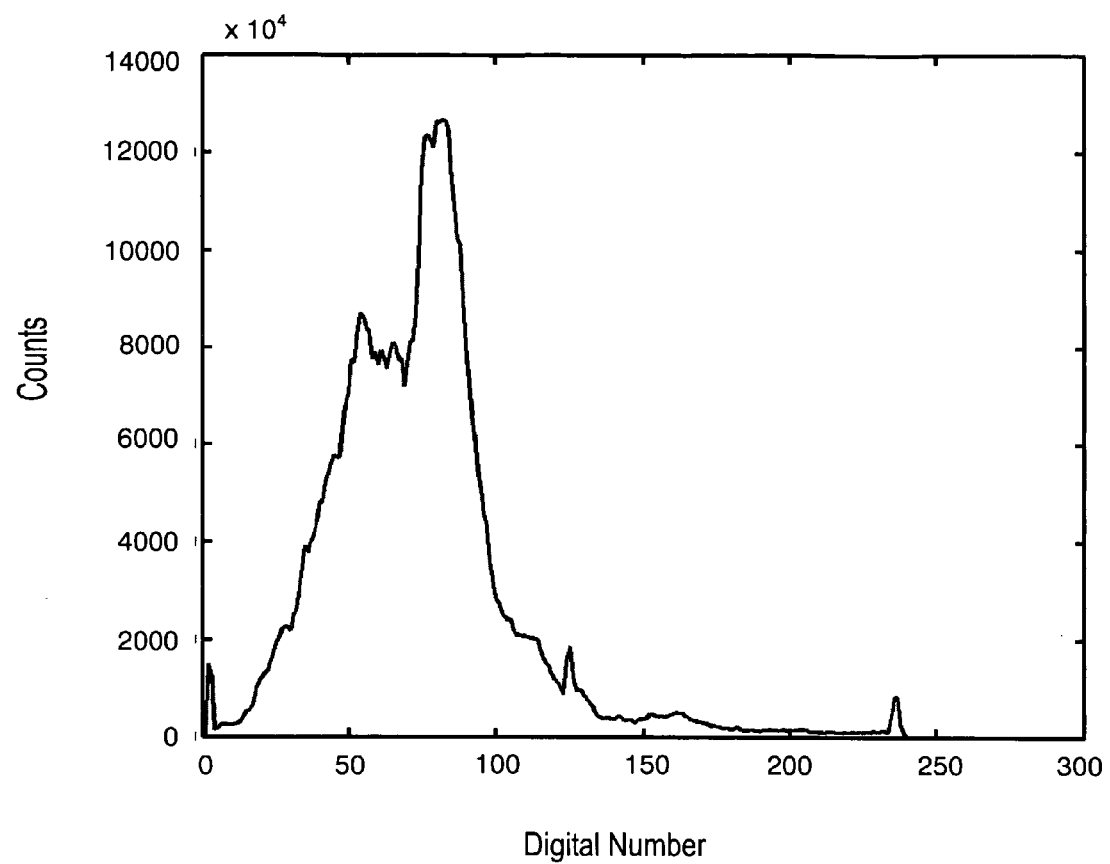
Figure 11C:
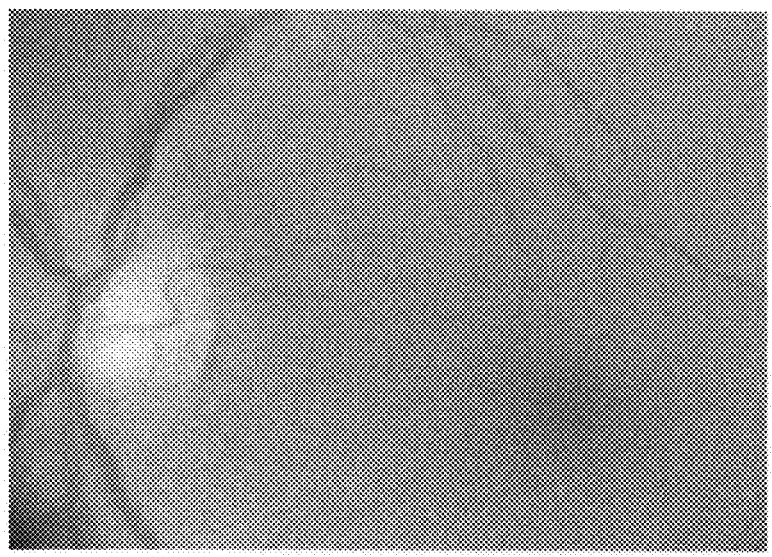
Figure 11D:
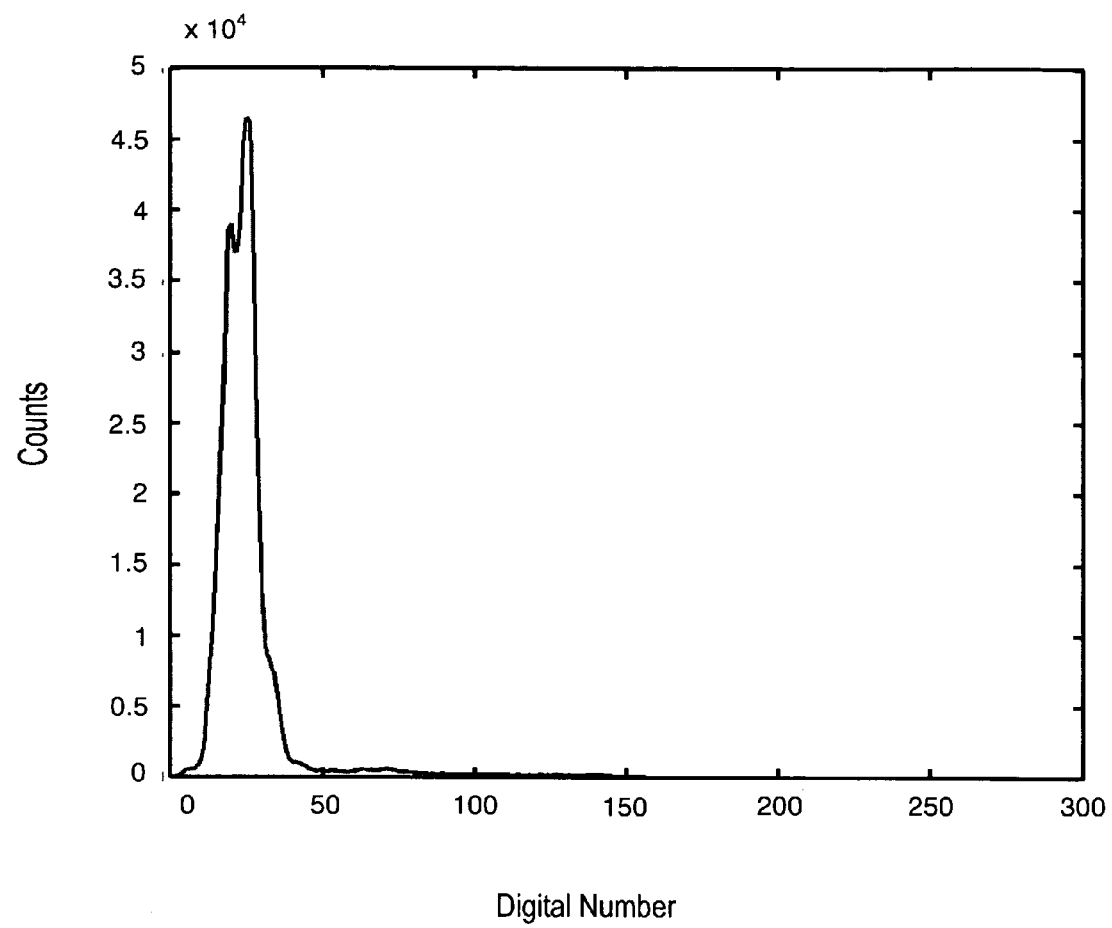

Referring now to FIG. 11A, an image is illustrated that has been digitized using a custom look up table according to the present invention. For comparison, FIG. 11C illustrates an image of the same subject digitized using a traditional linear LUT image. FIG. 11B illustrates the histogram for the image shown in FIG. 11A, whereas FIG. 11D illustrates the histogram for the image shown in FIG. 11C. Note that the image of FIG. 11A makes better use of the available gray level values than does the one of FIG. 11C. This fact is reflected in the higher contrast seen in the image.

Figure 12A:
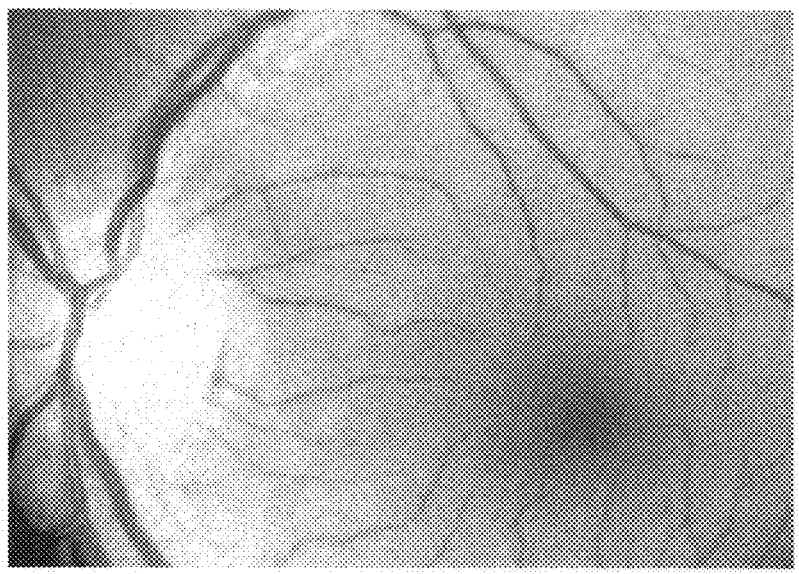
FIGS. 12A-12D illustrate retinal images taken using LUT's that are targeted for analyzing various tissue classes according to the present invention, or to produce a maximum entropy image.
Figure 12B:
Figure 12C:
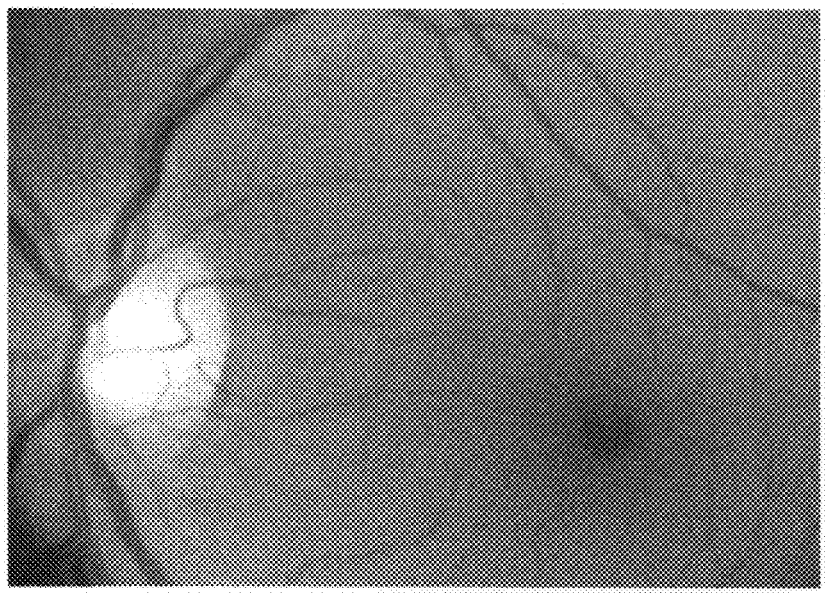
Figure 12D:
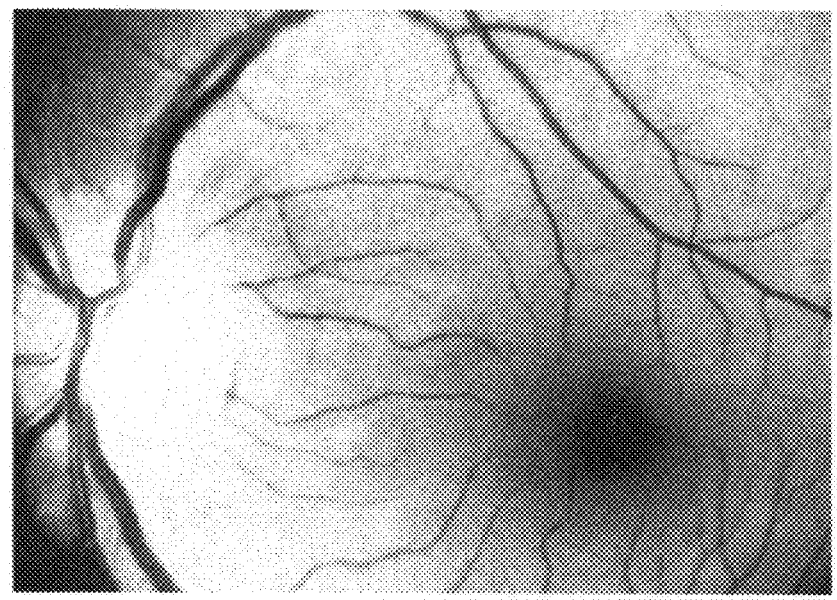

Referring now to FIGS. 12A-12C, preferred images for various tissue classes are illustrated. The custom LUT used to digitize the image of FIG. 12A is directed toward providing good visualization of the macula portion of the retina. The custom LUT used to digitize the image of FIG. 12B is directed toward providing good visualization of the retinal vessel. The custom LUT used to digitize the image of FIG. 12C is directed toward providing good visualization of the optic disc portion of the retina. FIG. 12D illustrates, for purposes of comparison with FIGS. 12A-12C, an image of the same subject digitized according to a maximum entropy digitization function.

One embodiment of the present invention incorporates CCDs with independently programmable LUTs in the A/D converter. The programmable LUT is loaded with the optimal LUT for the given target tissue and/or lesions via a user selectable interface. The varied nature of the different tissues and lesions found in the fundus, as an example of a blood perfused organ or vessel, is best imaged by use of a series of custom LUT's.

Digital cameras quantize the continuous analog video signal into a finite set of integer values. When this quantization occurs, information is lost due to the many-to-one mappings. Such mappings occur in three regions. Two of these regions are at the high intensity (overload or saturation) and low intensity (dark) ends of the dynamic range. Many-to-one mappings also occur within the quantization intervals. Decreasing the many-to-one mappings (in one region) will generally lead to lost information in another region. Most current digital cameras do not deal with these opposing constraints for minimizing information loss. Rather, they employ control algorithms that attempt to maintain signal levels within a range that prevents saturation at either end of the display or digitization spectrum. Attempts in the prior art to improve information quantization in intermediate ranges have not been effective, in particular, in situations where important detail may lie in those ranges. One example is the detection of disease. Another aspect of the present invention is a mapping function that is adjusted to create a balance between information lost in the different regions of quantization scale and optimization in spatially local regions in the scene.

Figures 13A, 13B:
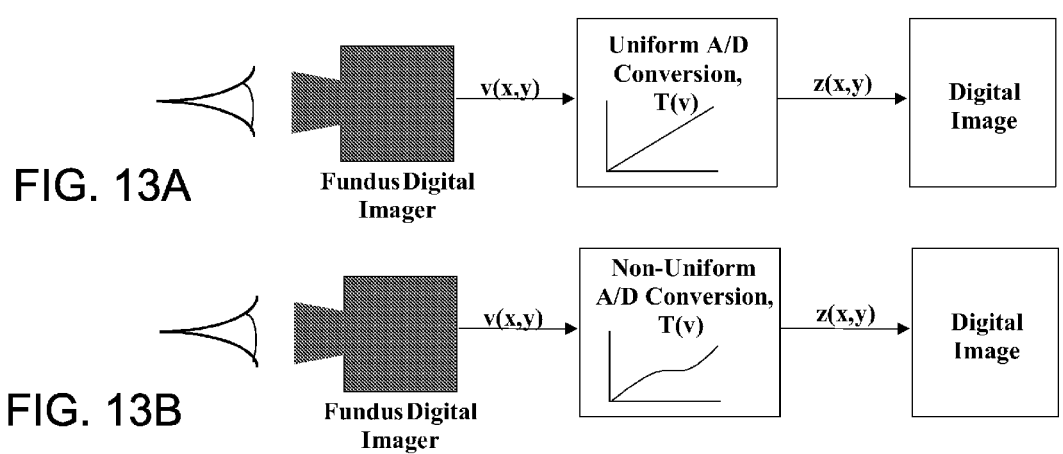
FIGS. 13A and 13B illustrate a block diagram of a video digitizing system comparing as linear LUT with an example of an enhanced entropy non-linear look up table according to an embodiment of the present invention.

Digital cameras employ an analog front end that maps the analog image signal onto an analog-to-digital converter. Referring now to FIGS. 13A and 13B, a video signal from a camera, v(x,y), is illustrated. For practical reasons, analog-to-digital converters nearly always employ uniform quantizers as illustrated in FIG. 13A. To quantize a video signal to have improved entropy, a mapping function, T(v), is used that non-uniformly quantizes an incoming signal in a manner that minimizes the information lost through quantization as is illustrated in FIG. 19B. Although this true maximum entropy mapping may not correspond to the most desirable image from quality viewpoint, a sub-optimal non-linear mapping can produce images of vastly improved quality as compared to that of the linear mapping. An aspect of the present invention is a fixed, non-linear custom LUT that produces a more useful and desirable fundus image is sought to replace the linear (fixed) LUT. Another aspect of the present invention is the use of the fixed custom LUT, which will in general produce images of higher quality than the traditional linear LUT. Another aspect of the present invention is a fixed LUT that avoids the need to seek the desired LUT dynamically. Another aspect of the present invention is that a fixed custom LUT avoids concerns over image interpretation. The custom LUT provides images of higher quality, with all images quantized in the same manner. The resulting intensity values therefore represent stationary qualities that can be compared from image to image and subject to subject.

Alternatively, a dynamic LUT can be implemented. If a dynamically varying custom LUT is implemented, the LUT is embedded as data in the header of the resulting digital image for further reference, and to aid in image interpretation if needed.

Information content is represented by the image's entropy. The Shannon entropy H, is commonly used as an information measure in communication problems. The image is modeled as a memoryless source, digitized to m bits, giving $N-2^m$ distinct gray levels where N is the number of bits used to store the information. The probability that a pixel has gray level k is $P(Z_k)$. Then $$H_s = -\sum_{k=0}^{N-1} p(z_k) \log_2 p(z_k) \text{ bits/pixel} \quad (1)$$

It is easy to illustrate that $0 \leq H \leq m$ bits/pixel with H=0 when only one gray level is present, and H=m when the gray levels are uniformly distributed. Thus, an image has the maximum information content when the histogram is uniformly distributed and entropy is maximized. It is between this extreme (maximum entropy) and the linear LUT that the desired custom non-linear LUT is sought.

According to an optional embodiment of the present invention standard digital histogram equalization is implemented in addition to the non-linear quantization that has been described herein. As practiced in the prior art, a histogram equalization is applied to the data after it has been quantized according to a linear quantization function. The prior art practice of histogram equalization serves to improve the mapping between a displayed digital image and the human vision system, allowing the viewer to see more detail. It is noted, however, that the information content of the image is not increased (refer to equation 1) by the prior art histogram equalization. This missing information represents the subtle variations that are often critical for visualization of early changes in the retina. Thus, the desire is to increase the overall information content of the image and retain these subtle intensity variations. Loss of information can optionally be mitigated according to practice of the present invention by in essence applying the equalization function directly to the analog video signal, v(x,y) through the use of a non-linear quantization function.

Figure 14:
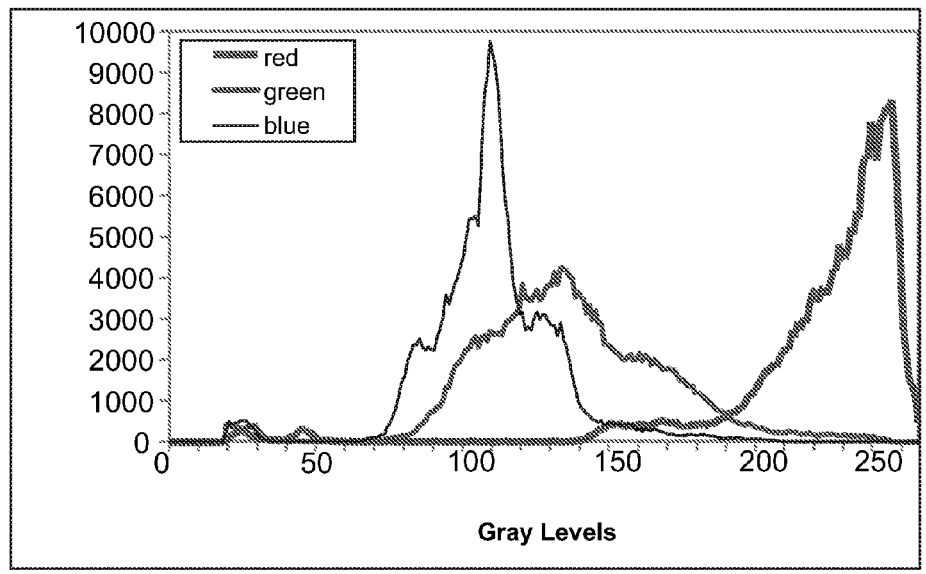
FIG. 14 illustrates a typical histogram for a color retinal image where no consideration is given to the difference in reflectance for each channel.
Figure 15:
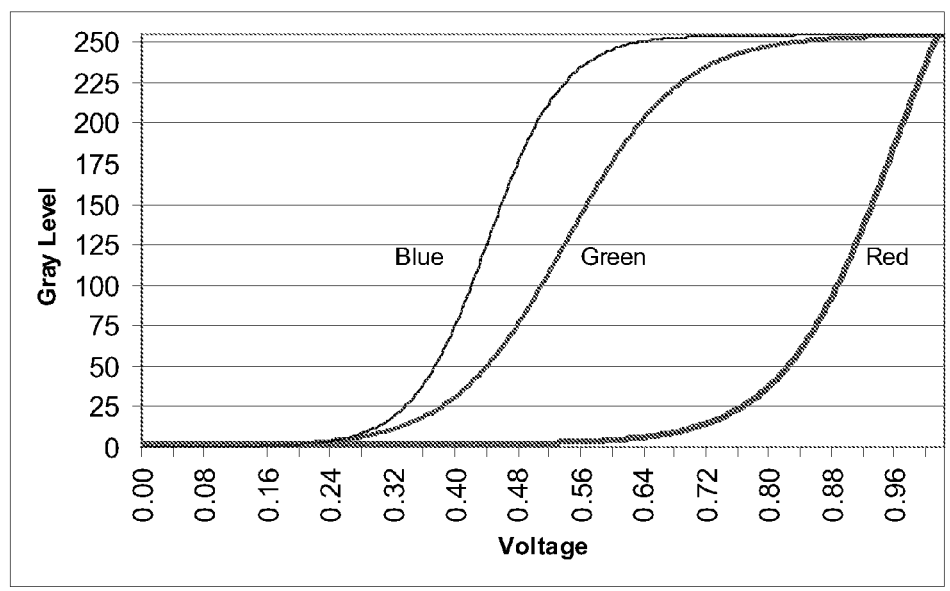
FIG. 15 illustrates a probability density function for analysis values derived from the same image shown in FIG. 14.

Because of the large variation in the reflectance between each of the RGB channels in retinal images, each channel is processed individually. Referring now to FIG. 14, a typical 8-bit histogram for a three color retinal image where no consideration is given to the difference in reflectance for each channel is illustrated. The red channel is often saturated (high pixel count with intensities greater than 250 with significant number of pixels of intensity greater than 255 clipped and reported as 255) because of the high reflectance in the red part of the spectrum (not an unexpected observation since the retina's reddish appearance is due to the perfusion of blood). Meanwhile, the green and blue channels have their intensities all in the lowest quartile of the histogram. The entropies, as calculated with equation 1, are 4.4, 4.6 and 4.1, respectively, for the R, G, and B channels. In spite of well documented knowledge of the retina's overwhelming reflectance in the red channel, none of the conventional digital cameras attempt to compensate for this phenomenon and a saturated red-channel and under-exposed green and blue channel (low information) result. Simply applying a gain, a capability available in some digital cameras, before the quantization would improve the entropy for the blue and green channels, but the red channel would suffer further saturation and loss of information. That is because of a bias in the retinal image toward the red band. In the context of imaging other things (besides blood perfused tissue) the bias would likely be different, but regardless of the bias, the affect in limiting increased entropy would be the same. In an enhanced entropy camera according to one embodiment of the present invention, a separate look-up table (LUT) is to be utilized for each channel, avoiding the above problem. Referring now to FIG. 15, the probability density functions are illustrated of the analog signal intensities for each channel given in FIG. 14.

As an example, an enhanced entropy camera according to an embodiment of the present invention is designed around a charge-coupled device (CCD) detector with programmable look-up table (LUT) in the analog-to-digital converter (A/D). As another example, an embodiment of the present invention employs three CCD detectors, a red, green, blue (RGB) dichroic splitter assembly, and three independently programmable A/D converters. According to the dichroic splitter embodiment, an RGB dichroic splitter (custom or commercially available) divides the incoming light into three paths. Unlike a traditional wide-band splitter that divides the incident light into multiple paths each with a fraction of the white light, the dichroic split is wavelength dependent. The dichroic sends all the light within a given band to one path, while the remaining light is passed in the other band. Thus, for spectral imaging applications (such as color photography), the dichroic avoids wasting light and is better suited for the light-limited situation encountered in retinal imaging. The RGB dichroic splitter assembly employs two dichroic splitters specifically designed with bands that match the red, green, and blue color channels used in color imaging.

According to still another embodiment of the present invention, a single masked CCD with custom programmable LUT's is incorporated into a chip. This diversity of implementation illustrates that the present invention may be practiced without limitation to the number of image capture devices, or any specific number of wavelength bands. A single band can be digitized according to the present invention, or multiple bands. One example of a multiple band configuration is the three color red, green, and blue (RGB) channel configuration that is commonly used in digital cameras.

In one embodiment of the present invention, an enhanced entropy camera is based on a 1K×1K detector with three CCD detectors. This configuration achieves full spatial resolution in each color channel. Single-CCD color cameras use one detector that has been masked. This mask divides the available camera pixels into red, green, and blue. The three colors may be distributed spatially in a dithered pattern. Of course, the present invention is not limited only to three color implementation, as more than three bands of light can be digitized using non-linear quantization by adding additional structures for additional desired bands.

Further, incorporating three separate CCD detectors allows each CCD to be independently controlled. The amount of light reflected from the fundus varies greatly in the three color channels. This is evidenced in the typically red-saturated fundus images found in standard fundus photography. Thus, each color channel will benefit from having a separate custom LUT. In this way the red bias of the image can be removed as an impediment to increasing the entropy of the image. The use of three independent CCD detectors has been demonstrated as an effective way to implement this embodiment. Further, the multiple CCD approach also allows for independent exposure adjustment.

Figure 16:
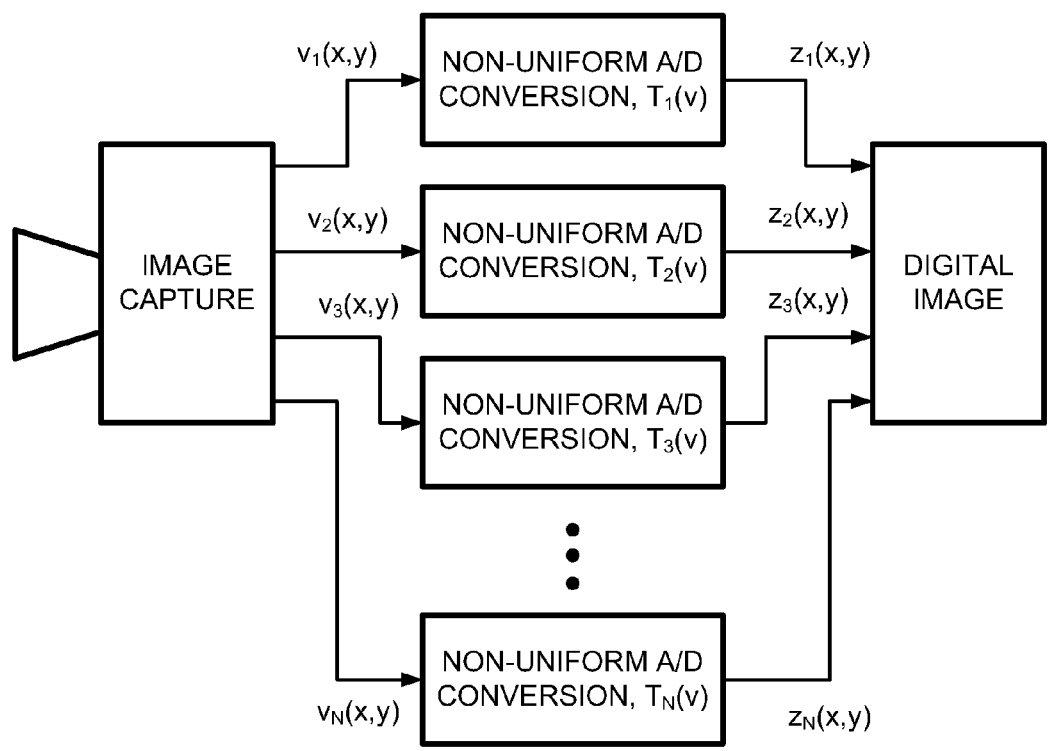
FIG. 16 schematically illustrates an imager having independent LUT's for each of multiple bands.

Referring to FIG. 16, an imager having independent LUT's for each of multiple bands is schematically illustrated. The number of bands N is any number, two or more. The non-linear digitization functions are generally distinct for each band. If desired some bands may have the same digitization function.

One aspect of the present invention is the ability to employ a custom LUT in the quantization process. Specifically, this capability amounts to the ability to specify and modify the function used to relate the analog signal to digital number conversion. Although a custom A/D with fixed LUT may be fabricated and falls within the practice of the present invention, this approach doesn't allow for changes to the desired LUT and would inhibit re-programming of the imager to enhance the image. Multiple custom A/D converters, each with a different LUT, is also an alternate embodiment. The use of a programmable LUT in the A/D converter allows the custom LUT to simply be loaded. Further, the programmable LUT approach allows for changes to the custom LUT as desired.

Finally, the variable nature of the different subjects of interest (tissues and lesions in the exemplary case of imaging the fundus) will likely require a series of custom LUTs. The programmable LUT design allows the LUT to be changed during use via software control. Thus, if the desire is to image the optic disc, the user could simply select 'optic disc' from the interface and the associated custom LUT would be loaded. Likewise, custom LUTs for the other tissues and lesions could be selected and loaded in real time. This agility to adapt the LUT on the fly based on the subject being analyzed in the image extends to the need to analyze any sort of image (e.g., remote sensing) to pick out multiple features having entirely different optical reflectance and absorption characteristics.

Another aspect of the present invention is an ability to mate to a fundus camera, for example, a Zeiss FF5. The fundus camera typically offers a viewing port and a separate imaging port for the enhanced entropy camera. This two-port design facilitates alignment and focus of the fundus camera.

A set of custom relay optics is used for an enhanced entropy camera according to this embodiment. These relay optics allow an enhanced entropy camera to optically couple to the fundus camera so as to ensure no loss in system performance.

It will be apparent to those skilled in the art that other variations in the camera and process of data from the camera are possible without departing from the scope of the invention as disclosed. For example, any type of digital camera may be used without restriction either to the number of pixels being used, or the aspect ratio, or the number of bits per pixel. Practice of the present invention is applicable for use with most all types of image capture devices.

The present invention has been described in terms of preferred embodiments, however, it will be appreciated that various modifications and improvements may be made to the described embodiments without departing from the scope of the invention.

What is claimed is:

1. A camera for producing a digital image signal having enhanced entropy, the camera comprising:
    light characteristic sensor producing an output;
    an image capture device;
    a programmable analog-to-digital converter connected to receive an image from the image capture device, the converter being programmed to quantize according to a non-linear quantization function selected based on the output of the light characteristic sensor;
    digital storage for receiving a digitized image signal from the converter, the digital image signal having enhanced entropy.

2. The camera of claim 1, wherein the output of the light characteristic sensor is indicative of color.

3. The camera of claim 1, wherein the output of the light characteristic sensor is indicative of intensity.

4. The camera of claim 1, wherein the non-linear quantization function comprises a non-linear look up table.

5. The camera of claim 1, wherein each of the non-linear quantization functions comprises a distinct non-linear look up table for each of red, green, and blue color channels.

6. The camera of claim 1, wherein each channel is balanced independently.

7. The camera of claim 1, wherein the exposure of each channel is adjusted independently.

8. The camera of claim 1, wherein the non-linear quantization function is intermediate between a linear function and a maximum entropy function.

9. A camera for producing a digital image of the fundus of an eye having enhanced entropy, the camera comprising:
    a fundus camera;
    an image capture device optically coupled to the fundus camera;
    a programmable analog-to-digital converter connected to receive an image from the image capture device, the converter being programmed to quantize each of plural spectral bands according to a respective non-linear quantization function, the respective non-linear quantization functions being substantially different from one another; and
    digital storage for receiving a digitized image signal from the converter, the digital image signal having enhanced entropy.

10. The camera of claim 9, wherein the respective non-linear quantization functions are selected so as to suppress the red content of the digital image signal.

* * * * *